(12) United States Patent  
Lukay et al.

(10) Patent No.: US 8,763,776 B2
(45) Date of Patent: Jul. 1, 2014

(54) COUPLER FOR VISCOMETER BOB SHAFT

(75) Inventors: Richard Lukay, Houston, TX (US); John Norwood, Houston, TX (US)

(73) Assignee: OPI Testing Equipment, Inc., Houston, TX (US)

( * ) Notice: Subject to any disclaimer, the term of this patent is extended or adjusted under 35 U.S.C. 154(b) by 416 days.

(21) Appl. No.: 13/124,371

(22) PCT Filed: Oct. 16, 2009

(86) PCT No.: PCT/US2009/060987
§ 371 (c)(1),
(2), (4) Date: Apr. 14, 2011

(87) PCT Pub. No.: WO2010/045544
PCT Pub. Date: Apr. 22, 2010

(65) Prior Publication Data
US 2011/0198187 A1  Aug. 18, 2011

Related U.S. Application Data

(60) Provisional application No. 61/106,089, filed on Oct. 16, 2008.

(51) Int. Cl.
*F16D 27/14* (2006.01)

(52) U.S. Cl.
USPC .................................................. 192/84.1

(58) Field of Classification Search
USPC ............ 29/402.08, 402.01, 402.03, 428, 744; 192/84.1; 72/54.32, 54.39, 54.35; 702/43
See application file for complete search history.

(56) References Cited

U.S. PATENT DOCUMENTS 4,899,576 A   2/1990   November et al.

FOREIGN PATENT DOCUMENTS

JP   H11-148894   6/1999

OTHER PUBLICATIONS

International Search Report and Written Opinion of the International Searching Authority issued for PCT/US2009/060987 on May 31, 2010.

*Primary Examiner* — John C Hong
(74) *Attorney, Agent, or Firm* — Kelling Patents & Trademarks, LLC; Kenneth A. Keeling; Melissa M. Martinez

(57) ABSTRACT

A coupler for attaching a lower segment of a viscometer bob shaft to an upper segment of a viscometer bob shaft includes an upper assembly connected to the upper segment, a lower assembly connected to the lower segment, a magnetic coupler, and a rotation connection.

18 Claims, 8 Drawing Sheets

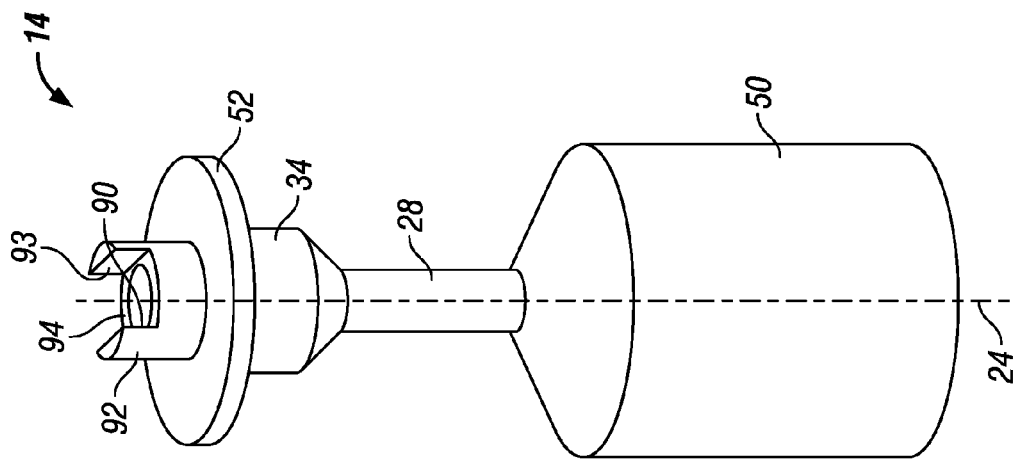
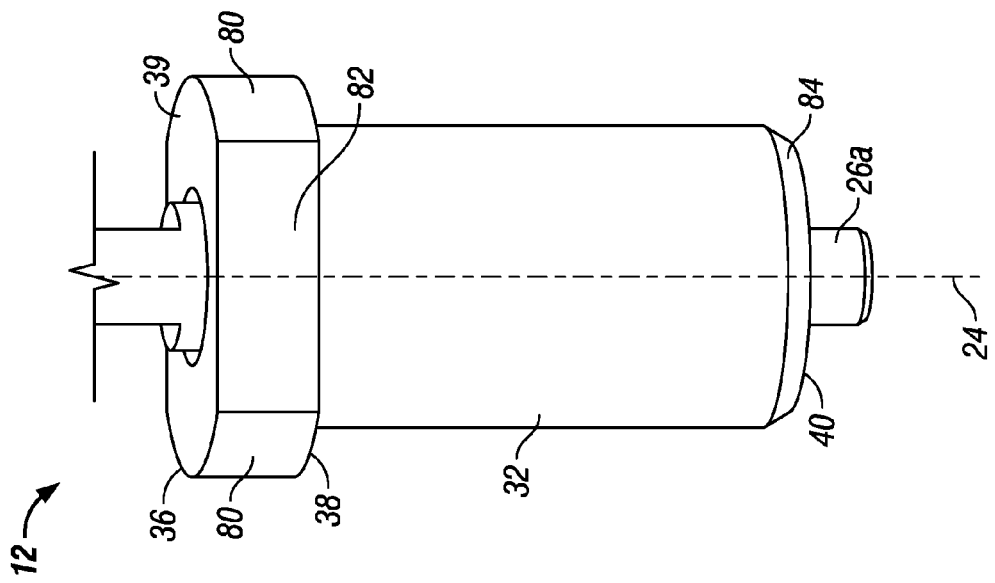

COUPLER FOR VISCOMETER BOB SHAFT

CROSS-REFERENCE TO RELATED APPLICATIONS

This application claims the benefit of U.S. provisional application Ser. No. 61/106,089 filed on Oct. 16, 2008, which application is incorporated herein by reference as if reproduced in full below.

STATEMENT REGARDING FEDERALLY SPONSORED RESEARCH OR DEVELOPMENT

Not Applicable.

BACKGROUND

1. Field of the Invention

The present invention relates generally to viscometers and more particularly to a coupler for providing connection of an upper segment and a lower segment of a bob shaft of a co-axial viscometer.

2. Description of the Related Art

Rotating viscometers include, among other things, a bob suspended from a bob shaft, and a torque-measuring device. In operation the bob is positioned in a sample cup containing a sample fluid. The fluid sample is rotated in relation to the bob by rotation of the sample cup or a sleeve in order to determine properties of the sample fluid.

It is necessary from time to time to clean the bob, change the bob type, replace the bob, or repair the bob. The bob is commonly attached to the bob shaft through use of threading so that the bob is screwed on and off the bob shaft for cleaning, replacement, or repair. This prior art attachment method creates the possibility of human error including over and under tightening during replacement of a bob. Over tightening of a bob to a bob shaft can lead to seizure of the bob to the bob shaft as well as to the sensing parts of the equipment. Under tightening of a bob to a bob shaft can lead to release of the bob during operation. This prior art attachment can also lead to damage to the bob and/or bob shaft including damage to the threading itself.

Another prior art method of bob attachment is a taper bore fit of the bob shaft in a hollow bob. This attachment method creates the possibility of the bob falling off and even the potential of rupture or explosion if fluid gets trapped inside the hollow bob and is heated.

Exemplary rotating viscometers having bob shafts are described in U.S. Pat. No. 6,070,457 to Robinson, U.S. Pat. No. 6,571,610 to Raffer, U.S. Pat. No. 6,691,559 to Robinson, U.S. Pat. No. 6,951,127 to Hongfeng, U.S. Pat. No. 6,938,474 to Hongfeng and U.S. Pat. No. 7,287,416 to Hongfeng. The identified patents disclose various ways of attaching a bob to a bob shaft and/or a torsion wire, attaching a bob by use of threading of the bob and the bob shaft or by constructing the bob integral with the bob shaft.

SUMMARY OF THE INVENTION

A coupler for attaching a lower segment of a viscometer bob shaft to an upper segment of a viscometer bob shaft is provided. The coupler includes an upper assembly connected to an upper shaft segment, a lower assembly connected to a lower shaft segment, a magnetic coupler, and a rotation connection. The magnetic coupler maintains contact of the lower assembly with the upper assembly. The rotation connection rotationally couples the upper assembly and the lower assembly to provide non-slipping transfer of rotational force between the upper and lower magnetic assemblies.

BRIEF DESCRIPTION OF THE DRAWINGS

For a more complete understanding of exemplary embodiments of the invention, reference is made to the following Detailed Description taken in conjunction with the accompanying drawings, in which:

FIG. 7 is a perspective view of the upper assembly of the alternative coupler of FIG. 8.

FIG. 8 is a perspective view of the lower assembly of the alternative coupler of FIG. 8.

DETAILED DESCRIPTION

Figure 1:
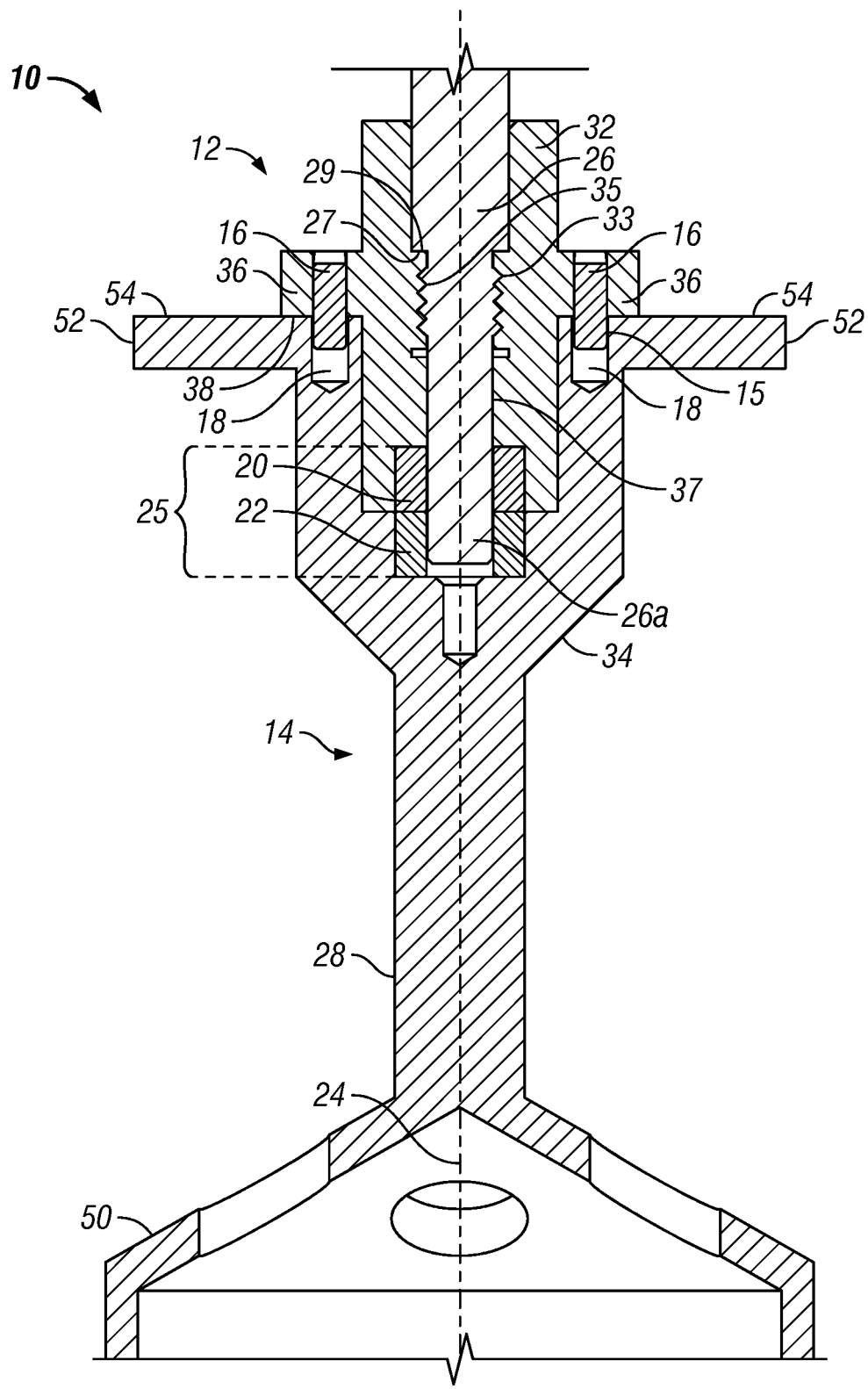
FIG. 1 is a cross-sectional view of a coupler.

Embodiments of the invention are best understood by referring to the drawings, like numerals being used for like and corresponding parts of the various drawings.

This disclosure relates to a coupler 10 between bob shaft segments of a viscometer. The description herein relates to a typical co-axial rotating viscometer, but the invention is not limited to use with the viscometer described herein nor to any particular viscometer.

Figure 3:
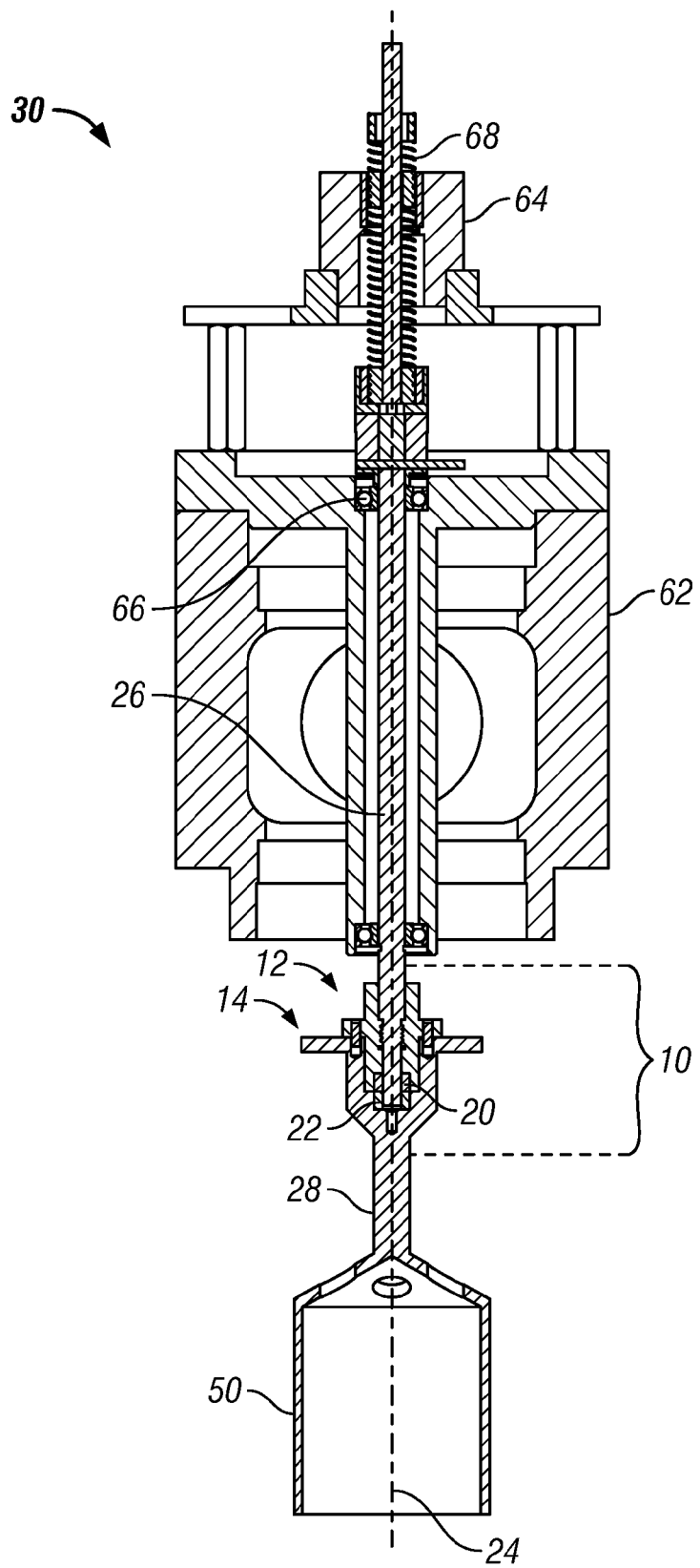
FIG. 3 is a cross-sectional view of a coupler installed on a coaxial viscometer.

Referring to FIG. 3, a coupler 10 is shown attached to a coaxial viscometer 30. Viscometer 30 is a coaxial viscometer having a viscometer body 62, a torsion spring assembly 64, bearings 66, and a torsion spring 68. An upper bob shaft 26 extends through viscometer body 62 and functionally engages torsion spring assembly 64. The torsion spring 68 of torsion spring assembly 64 biases upper bob shaft 26 toward an initial position and resists rotational movement of upper bob shaft 26.

Bob shaft bearings 66 retain upper bob shaft 26 in vertical alignment while minimizing the frictional resistance to rotation of upper bob shaft 26. Viscometer 30, viscometer body 62, torsion spring assembly 64, bearings 66 and torsion spring 68 are exemplary only. The coupler 10 of the present invention may be practiced with other viscometers, rheometers, or the like.

Referring to FIG. 1, an exemplary coupler 10 is depicted. Coupler 10 includes an upper assembly 12, a lower assembly 14, a magnetic coupler 25, and a rotation connection 15.

A common axis 24 is shown for descriptive purposes. Axis 24 is the common axis for upper assembly 12 and lower assembly 14 when upper assembly 12 and lower assembly 14 are in coupled orientation. Coupled orientation means generally that upper assembly 12 and lower assembly 14 are magnetically attached and rotationally coupled.

Referring to FIG. 1, an exemplary magnetic coupler 25 comprises a magnet 20 and a magnet 22. Upper assembly 12 includes magnet 20. Lower assembly 14 includes magnet 22. Magnet 20 and magnet 22 are positioned such that they are aligned with each other when upper assembly 12 is in coupled orientation with lower assembly 14. Magnet 20 and magnet 22 accordingly engage each other.

A rotation connection 15 comprises an interface between upper assembly 12 and lower assembly 14 that rotationally couples upper assembly 12 and lower assembly 14. Rotation connection 15 prevents upper assembly 12 and lower assembly 14 from rotating about axis 24 independently of each other. Rotation connection 15 provides non-slipping transfer of rotational force between lower assembly 14 and upper assembly 12.

An exemplary rotation connection 15 is depicted in FIG. 1. Rotation connection 15 includes insert pins 16 and pin receivers 18. Upper assembly 12 includes a flange 36. Flange 36 has a lower face 38. Upper assembly 12 includes insert pins 16 extending from lower face 38 for functionally engaging pin receivers 18 in lower assembly 14. Lower assembly includes a flange 52. Flange 52 has an upper face 54. Lower assembly 14 includes pin receivers 18, sized and aligned to receive insert pins 16. In coupled orientation lower face 38 is aligned with upper face 54.

Figure 2:
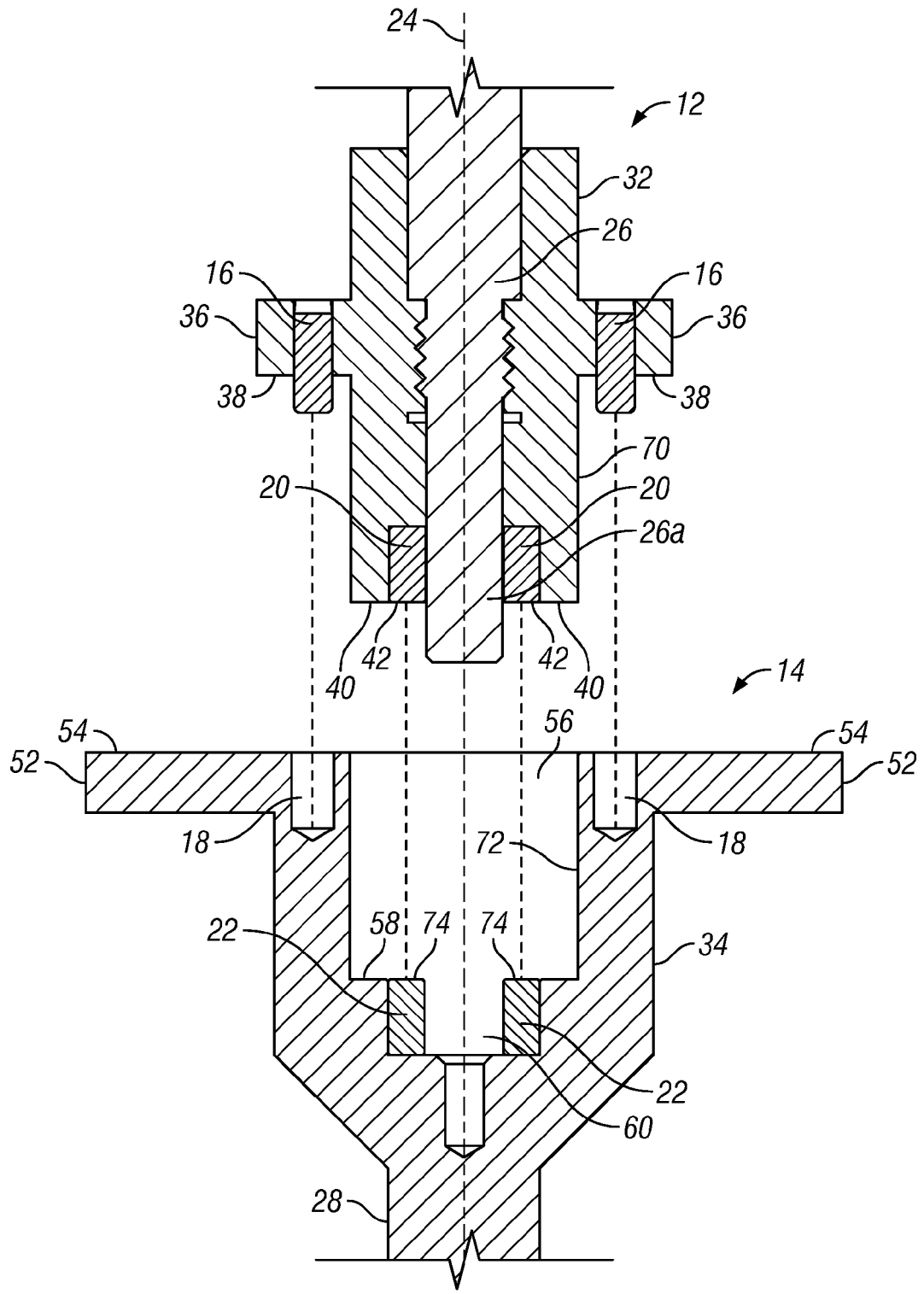
FIG. 2 is an exploded cross-sectional view of a coupler.

The exploded view of FIG. 2 shows upper assembly 12 and lower assembly 14 detached from each other, but aligned for attachment.

Figure 5:
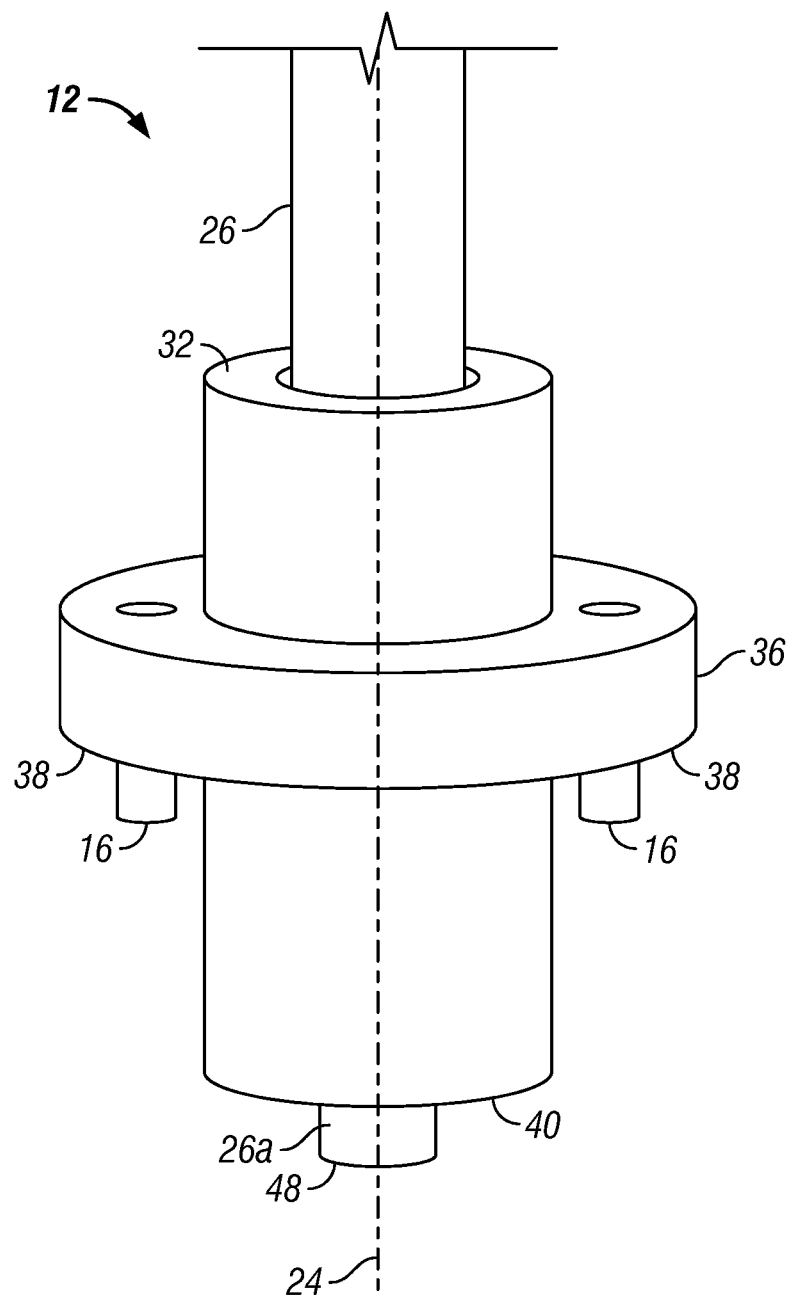
FIG. 5 is a perspective view of an upper assembly.

Referring to FIG. 5, upper assembly 12 is formed generally as a hollow upper body 32, having an outwardly extending upper assembly flange 36. Upper body 32 and upper assembly flange 36 are coaxially aligned with axis 24. Upper body 32 is substantially cylindrical.

Upper assembly flange 36 includes a lower face 38. Two engagement insert pins 16 extend downwardly from upper assembly flange 36, generally parallel to common axis 24.

A magnet 20 is provided in upper body 32 as shown in FIG. 2. In an exemplary embodiment of the invention magnet 20 is formed generally as a hollow cylinder concentrically oriented about axis 24. Lower surface 42 of magnet 20 lies below lower surface 40 of upper body 32. In an alternative embodiment lower surface 42 of magnet 20 lies in a plane with lower surface 40 of upper body 32. Magnet 20 is fixedly attached to coupler upper body 32. Such attachment may be by press fitting, glue or other appropriate means.

Referring to FIG. 1, a portion of upper bob shaft 26 extends through upper assembly 12. Upper bob shaft 26 is aligned with common axis 24. Upper bob shaft 26 includes a reduced diameter upper bob shaft segment 26a defining a shoulder 27 in bob shaft 26. Upper bob shaft segment 26a extends downwardly from upper bob shaft 26, through upper body 32, and is concentric with common axis 24. Shoulder 27 substantially abuts a corresponding shoulder 29 in upper body 32. Shoulders 27 and 29 are substantially perpendicular to axis 24. Shoulders 27 and 29 are aligned upon attachment of upper body 32 with bob shaft 26. Alignment of shoulders 27 and 29 helps to ensure that upper assembly 12 is concentrically aligned about axis 24.

Upper bob shaft segment 26a has left-handed threading 33 on its exterior surface 37. Upper body 32 is fixedly attached to upper bob shaft segment 26a by means of corresponding left-hand threading 35. Left-handed threading is constructed so that normal right hand rotation of bob 50 will bias the threading toward an engaged position. Alternative attachment means include, but are not limited to, press fitting, threaded engagement, or other means.

Figure 4:
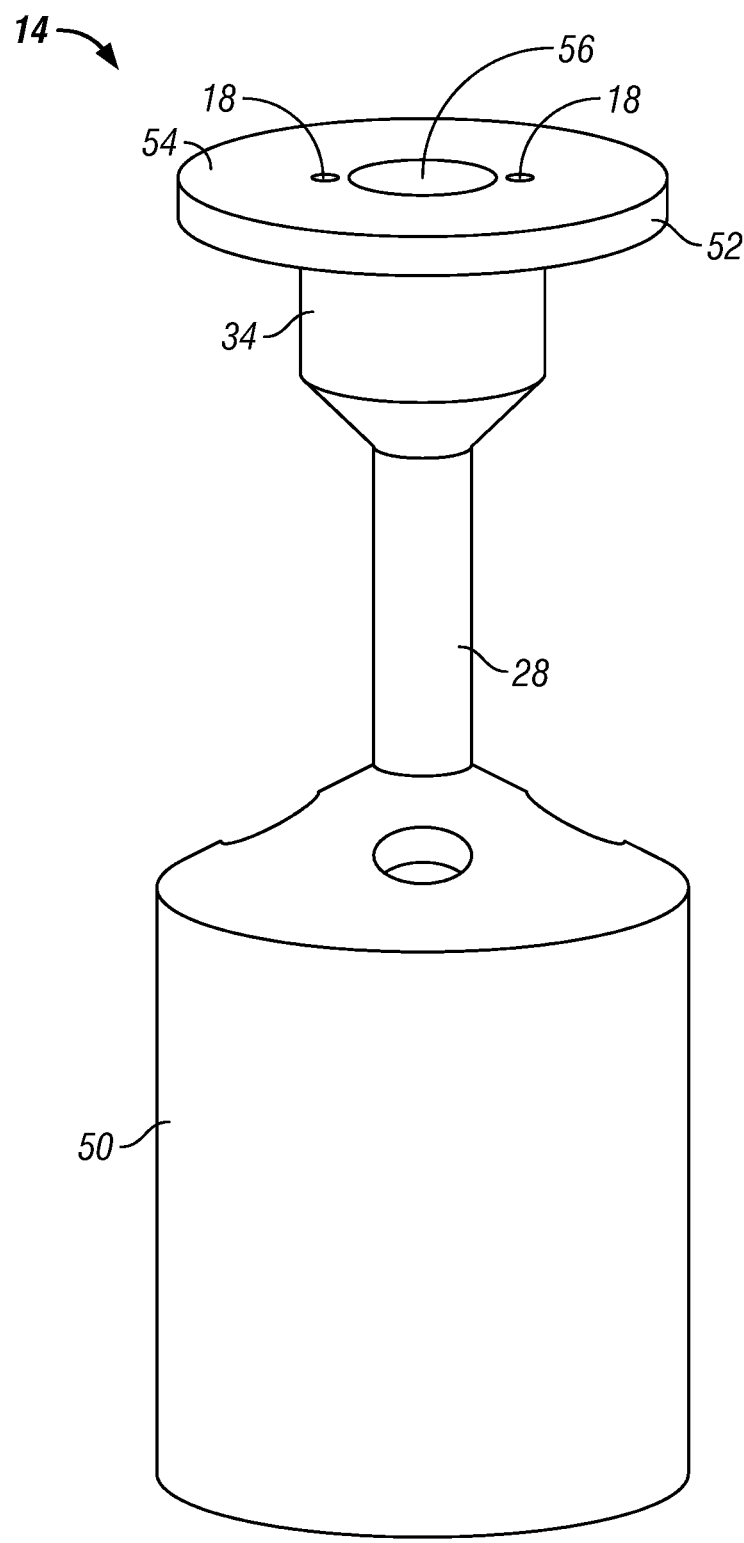
FIG. 4 is a perspective view of a lower assembly.

Referring to FIG. 4, lower assembly 14 is formed generally as a lower body 34 having an outwardly extending lower assembly flange 52, pin receivers 18, and magnet 22. Lower body 34 and lower assembly flange 52 are coaxially aligned with axis 24. Lower body 34 is substantially cylindrical.

Lower assembly 14 is connected to lower bob shaft 28, which is in turn connected to bob 50. Lower bob shaft 28 extends downwardly from body 34. A bob 50 is attached to lower bob shaft 28 distal lower body 34. Lower body 34, lower assembly flange 52, lower bob shaft 28, and bob 50 are coaxially aligned with axis 24. Lower bob shaft 28 may be an elongated rod attached at its top to the lower body 34. Bob 50 is attached at its upper end to the bottom of lower bob shaft 28. Such attachment may be fixed or removable, such as by threading.

Two pin receivers 18 are provided in lower body 34. Pin receivers 18 and insert pins 16 are sized and structured so that insert pins 16 may be received in pin receivers 18 when upper face 54 of lower assembly flange 52 is positioned adjacent lower face 38 of upper assembly flange 36.

Lower body 34 is generally cylindrical with a countersunk socket 56 in its upper face 54. Socket 56 is a cylindrical recess. Socket 56 and coupler upper body 32 are sized and structured such that at least a portion of upper body 32 may be received into and removed from socket 56 by sliding movement. In the exemplary embodiment shown, socket 56 is cylindrical and concentrically oriented about common axis 24.

In an exemplary embodiment the depth of socket 56 is between one and two times the diameter of upper body 32 to facilitate alignment of upper body 32 and lower body 34.

Socket 56 is partially defined by a lower socket surface 58 and interior walls 72. A lower magnet 22 is provided in lower body 34. Magnet 22 is formed generally as a hollow cylinder coaxially aligned with axis 24. Upper surface 74 of magnet 22 lies above lower socket surface 58. In an alternative embodiment upper surface 74 of magnet 22 lies in a plane with lower socket surface 58. Magnet 22 is fixedly attached to lower body 34. Such attachment may be by press fitting, glue or other appropriate means.

An alignment opening 60 is provided in lower socket surface 58. Alignment opening 60 is coaxially aligned with axis 24. Alignment opening 60 is sized and structured to receive reduced diameter upper bob shaft segment 26a upon sliding engagement of upper body 32 with socket 56 of lower body 34.

Coupled orientation of coupler 10 is achieved by attaching lower assembly 14 to upper assembly 12. In the exemplary embodiment of FIGS. 1-5, insert pins 16 are aligned with pin receivers 18. Reduced diameter upper bob shaft segment 26a is aligned with alignment opening 60. Lower assembly 14 is pushed onto upper body 32 with upper body 32 received in socket 56 and insert pins 16 received in pin receivers 18.

In coupled orientation, lower surface 42 of upper magnet 20 abuts upper surface 74 of lower magnet 22. Lower face 38 of upper assembly flange 36 lies proximate top face 54 of lower assembly flange 52.

Reduced diameter upper bob shaft segment 26a is positioned in alignment opening 60 and helps to ensure that lower assembly 14 is coaxially aligned with common axis 24. Upper assembly 12 is snugly positioned in socket 56, thereby aiding in the overall stability of upper assembly 12 in relation to lower assembly 14.

In coupled orientation, magnet 20 and magnet 22 are aligned with magnetic orientation such that the magnets 20 and 22 are magnetically attracted to each other. Magnet 20 and magnet 22 are so sized and positioned that they are substantially aligned when upper body 32 is received in socket 56. Magnet 20 and magnet 22 are structured to maintain connection of upper assembly 12 with lower assembly 14 in vertical orientation with respect to axis 24, when upper body 32 is received in socket 56. Connected in vertical orientation may also be described as connected linearly with respect to axis 24.

The magnetic attraction force between magnet 20 and magnet 22 is stronger than the gravitational force on lower assembly 14, and is thereby sufficient to maintain contact of upper assembly 12 with lower assembly 14. Such attraction may be overcome by a user having normal strength by pulling lower assembly 14 away from upper assembly 12. Such removal of lower assembly 14 from upper assembly 12 minimizes damage to the upper bob shaft 26, lower bob shaft 28 or other parts of viscometer 30 during attachment and removal of lower assembly 14 from upper assembly 12.

In coupled orientation, any rotational force exerted on lower assembly 14 will be transmitted to upper assembly 12 through rotation connection 15. In the exemplary embodiment of FIGS. 1-5, pin receivers 18 transmit rotational force to pins 16. Pins 16 transmit rotational force to upper assembly 12. Accordingly, upper assembly 12 will rotate with lower assembly 14. Insert pins 16 and pin receivers 18 are constructed with close tolerance to allow rotational force asserted on lower assembly to be transmitted to upper assembly 12 without slippage. Insert pins 16 are constructed of sufficient thickness to prevent breakage of the insert pins 16 when rotational force is applied to lower assembly 14.

Operation

In operation of viscometer 30, a sample cup (not shown) containing a sample of fluid to be tested (not shown) is positioned such that bob 50 extends into the sample cup. A rotational force is applied to the sample fluid, whether by rotation of the cup or a sleeve coaxially aligned with bob 50. The rotational force of the fluid sample is resisted by friction at the surfaces of bob 50 and a rotational force is exerted on the surfaces of bob 50. The rotational force is transmitted to lower bob shaft 28 and consequently to lower assembly 14, upper assembly 12, upper bob shaft 26 and torsion spring 68. Such rotational force is quantified by torsion spring assembly 64 and transmitted as output.

Alternative Embodiment

Figure 6:
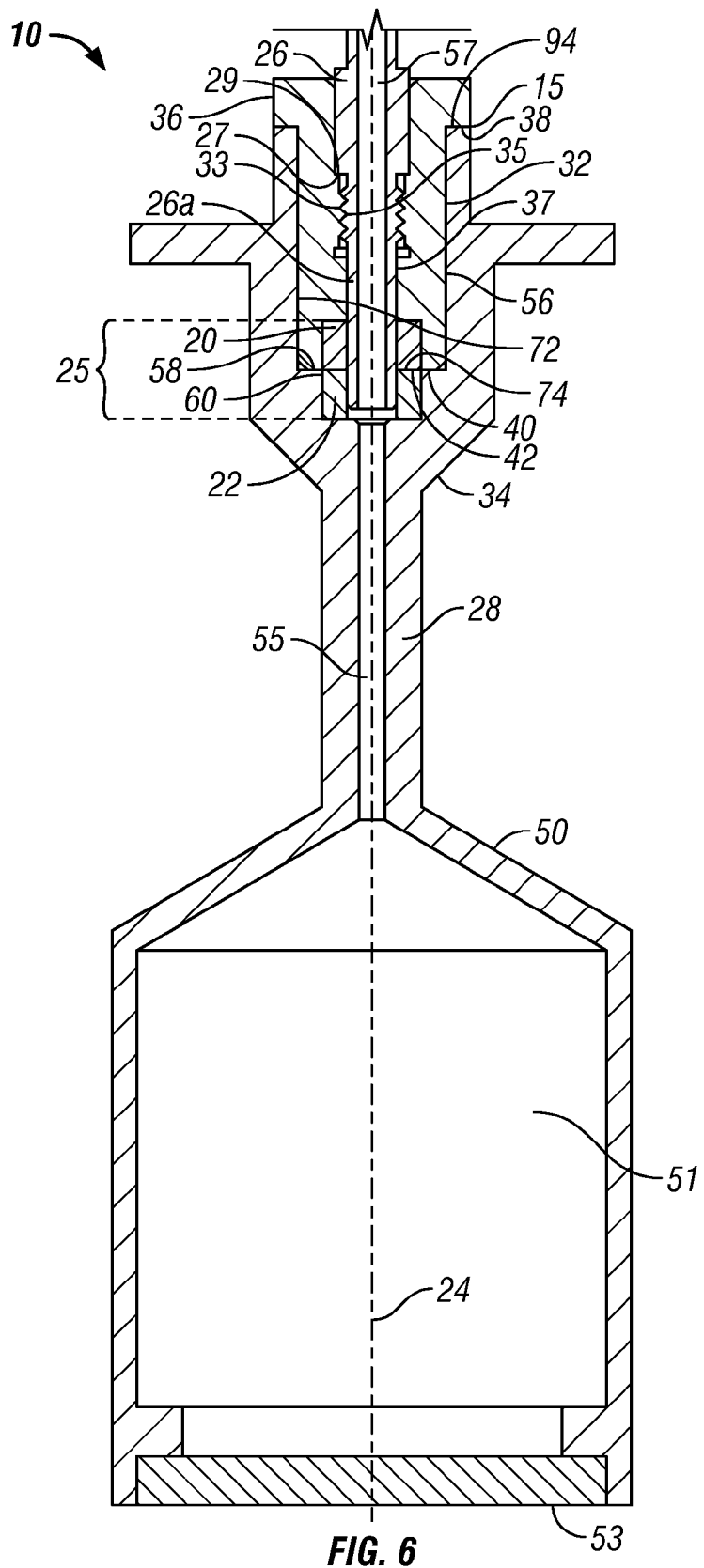
FIG. 6 is a cross-sectional view of an alternative coupler.

Referring to FIGS. 6-8, an alternative embodiment of coupler 10 is depicted. Coupler 10 includes an alternate upper assembly 12, an alternate lower assembly 14, an alternate magnetic coupler 25, and an alternate rotation connection 15.

An exemplary rotation connection 15 is shown in FIG. 6. Rotation connection 15 includes flange 36 on upper assembly 12 and a channel 90 in lower assembly 14. Flange 36 is formed and constructed to functionally engage channel 90. Engagement of flange 36 with channel 90 rotationally couples upper assembly 12 and lower assembly 14.

An exemplary magnetic coupler 25 is shown in FIG. 6. Upper assembly 12 includes a magnet 20. Lower assembly 14 includes a magnet 22. Magnet 20 and magnet 22 are positioned such that they are aligned with each other when upper assembly 12 is adjacent lower assembly 14 and flange 36 is engaged in channel 90. Magnet 20 and magnet 22 accordingly engage each other.

Common axis 24 is the common axis for the upper bob shaft 26, lower bob shaft 28, upper assembly 12, and lower assembly 14.

Referring to FIG. 7, upper assembly 12 is formed generally as a hollow upper body 32, having an outwardly extending upper assembly flange 36. Upper assembly flange 36 and upper body 32 have a common upper surface 39. Upper body 32 and upper assembly flange 36 are coaxially aligned about axis 24. Upper body 32 has a bevel 84 at its lower edge. Reduced diameter upper bob shaft segment 26a extends from viscometer body 62 through upper body 32 and partially protrudes from upper body 32.

Upper flange 36 is sized and constructed to fit within channel 90, as described below, in lower assembly body 34. Upper flange 36 has rounded ends 80 and flat sides 82. In the exemplary embodiment two flat sides 82 are provided. Flat sides 82 are parallel to each other. The construction of upper flange 36 with at least one flat side may be referred to herein as a truncated flange. Upper assembly flange 36 has a lower face 38.

Referring to FIG. 6, a magnet 20 is provided at lower surface 40 of upper body 32. In an exemplary embodiment magnet 20 is formed generally as a hollow cylinder concentrically oriented about axis 24. Lower surface 42 of magnet 20 lies below lower surface 40 of upper body 32. In an alternative embodiment lower surface 42 of magnet 20 lies in a plane with lower surface 40 of upper body 32. Magnet 20 is fixedly attached to coupler upper body 32. Such attachment may be by press fitting, glue or other appropriate means.

Upper bob shaft 26 extends through upper assembly 12. Upper bob shaft 26 includes a reduced diameter upper bob shaft segment 26a defining a shoulder 27 in bob shaft 26. Upper bob shaft segment 26a extends downwardly from upper bob shaft 26, through upper body 32 concentrically with common axis 24. Shoulder 27 abuts a corresponding shoulder 29 in upper body 32. Shoulders 27 and 29 are perpendicular to axis 24. Alignment of shoulders 27 and 29 helps to ensure that upper assembly 12 is aligned with axis 24.

Upper bob shaft segment 26a has left-handed threading 33 on its exterior surface 37. Upper body 32 is fixedly attached to upper bob shaft segment 26a by means of corresponding left-hand threading 35. Left-handed threading is constructed so that normal right hand rotation of bob 50 will bias the threading toward an engaged position. Alternative attachment means include, but are not limited to, press fitting, threaded engagement, or other means. A hollow bore 57 extends through bob shaft 26.

Referring to FIG. 8, lower assembly 14 is formed generally as a lower body 34 having a channel 90, an outwardly extending lower assembly flange 52, and magnet 22 (shown in FIG. 6). Lower body 34 and lower assembly flange 52 are coaxially aligned with axis 24.

Channel 90 is formed and constructed in lower body 34 to slidably receive flange 36. Channel 90 is formed in the upper portion of lower body 34. Channel 90 has walls 92 and a partially arcuate lower face 94. Walls 92 have inner surfaces 93.

Lower body 34 is generally cylindrical with countersunk socket 56 extending inwardly from channel 90. Socket 56 is a cylindrical recess. Socket 56 and coupler upper body 32 are sized and structured such that upper body 32 may be received into and removed from socket 56 by sliding movement. In the exemplary embodiment shown, socket 56 is cylindrical and concentrically oriented about common axis 24.

In an exemplary embodiment the depth of socket 56 may be between one and two times the diameter of upper body 32 to facilitate alignment of lower body 34 with upper body 32. Upper body 32 is constructed with a height equivalent to the depth of socket 56 plus the thickness of flange 36. The thickness of flange 36 is the distance between lower face 38 and upper surface 39.

Countersunk socket 56 is partially defined by a lower socket surface 58 and interior walls 72. An alignment opening 60 is provided in lower socket surface 58. Alignment opening 60 is axially aligned with axis 24. Alignment opening 60 is sized and structured to receive lower magnet 22. Lower magnet 22 is provided in alignment opening 60. Magnet 22 is formed generally as a hollow cylinder coaxially aligned with axis 24. Upper surface 74 of magnet 22 lies slightly above lower socket surface 58. In an alternative embodiment upper surface 74 of magnet 22 lies in a plane with lower socket surface 58. Magnet 22 is fixedly attached to lower body 34. Such attachment may be by press fitting, glue or other appropriate means. Lower magnet 22 is sized and structured to receive the protruding portion of reduced diameter upper bob shaft segment 26a upon sliding engagement of upper body 32 with socket 56. Positioning reduced diameter upper bob shaft segment 26a into alignment opening 60 helps to ensure that lower assembly 14 is aligned along common axis 24.

Lower bob shaft 28 extends downwardly from lower body 34. In the exemplary embodiment bob 50 is an elongated hollow rod defining a central bore 55. Bob 50 is attached to lower bob shaft 28 distal lower body 34. Lower body 34, lower bob shaft 28, and bob 50 are coaxially aligned with axis 24. The attachment of bob 50 may be fixed or removable, such as by threading.

Referring to FIG. 6, bob 50 has a hollow interior 51. Fluid communication is allowed from hollow interior 51 through hollow bore 55 and bob shaft 28 to alignment opening 60. Fluid communication allows relief of pressure in hollow interior 51 during heating and cooling.

When coupler 10 is in coupled orientation, the protruding end of upper shaft segment 26a is received in magnet 22, upper body 32 is received in socket 56, and flange 36 is received in channel 90. Lower surface 42 of upper magnet 20 abuts upper surface 74 of lower magnet 22.

Rotation connection 15 is formed by receipt of flange 36 in channel 90. Lower face 38 of flange 36 lies proximate lower face 94 of channel 90. Flat sides 82 of upper flange 36 contact inner surfaces 93 of channel 90.

When flange 36 is received in channel 90, rotational force exerted on lower assembly 14 will be transmitted through rotation connection 15 to upper assembly 12. Specifically, inner surfaces 93 of sidewalls 92 will exert rotational force on flat sides 82 of flange 36. Flange 36 will exert rotational force on upper assembly 12. Accordingly, upper assembly 12 will rotate with lower assembly 14. Flange 36 and channel 90 are constructed with close tolerance to allow rotational force asserted on lower assembly 14 to be transmitted to upper assembly 12 without slippage. Flange 36 is constructed of sufficient thickness to prevent breakage of flange 36 when rotational force is applied to lower assembly 14.

Referring to FIG. 6, when coupler 10 is in coupled orientation, hollow bore 55 is in fluid connection with hollow bore 57. Hollow bore 55 and hollow bore 57 are formed and constructed to allow flow of gas from hollow interior 51 to hollow bore 57.

Referring to FIG. 6, when coupler 10 is in coupled orientation, magnetic coupler 25 magnetically links lower assembly 14 to upper assembly 12 such that the magnets 20 and 22 are magnetically attracted to each other. Magnet 20 and magnet 22 are so sized and positioned that they are substantially aligned when upper body 32 is received in socket 56. Such alignment maintains connection of upper assembly 12 with lower assembly 14 when upper body 32 is received in socket 56.

The magnetic attraction force between magnet 20 and magnet 22 is stronger than the gravitational force on lower assembly 14. Such attraction may be overcome by a user having normal strength by pulling lower assembly 14 away from upper assembly 12.

In the embodiment depicted in FIGS. 6 to 8, two flat sides 82 abut corresponding inner surfaces 93 of sidewalls 92 to transmit rotational force from lower assembly 14 to upper assembly 12. In an alternative embodiment, a single flat side 82 abutting a single inner surface 93 may be used to achieve the same result. In an alternative embodiment, more than two flat sides 82 may abut more that two surfaces 93 to achieve the same effect. In an alternative embodiment, the side 82 and the inner surface 93 need not be flat. Accordingly, the surface configurations that may be used for a rotation connection may comprise one or more abutting faces configured to cooperatively induce rotation of the upper assembly 12 when the lower assembly 14 is rotated.

In an alternative embodiment, the number and location of insert pins 16 and corresponding pin receivers 18 may vary from the embodiment described in FIGS. 1-5 may vary. A single pin 16 may be used. More than two pins 16 may be used. In an alternative embodiment, more pin receivers 18 than insert pins 16 may be used so long as alignment of each insert pin 16 with at least one pin receiver 18 may be achieved.

In an alternative embodiment upper body 32 may constructed in other than substantially cylindrical form. In an alternative embodiment socket 56 may be constructed in other than substantially cylindrical form.

In an alternative embodiment a segment of the external wall 70 of upper body 32 proximate received in lower body 34 is constructed in other than cylindrical form, such as a triangle, rectangular, hexagon or other configuration, and a corresponding segment of internal wall 72 of lower body 34 is provided with a corresponding non-cylindrical form, such that external wall 70 and the internal wall 72 closely fit along at least some surfaces. The interface between external wall 70 and internal wall 72 may function as rotation connection 15.

Magnets 20 and 22 may be constructed from any appropriate magnetic material. One or both of magnet 20 and magnet 22 may be an electromagnet. The number and location of magnets 20 and magnets 22 may be varied.

In an alternative embodiment a magnet is provided in only upper assembly 12 and lower assembly 14 is constructed with at least some magnetically attractive metal such that the magnet in upper assembly 12 attracts and holds the magnetically attractive metal of lower assembly 14. In an alternative embodiment a magnet is provided in only lower assembly 14 and upper assembly 12 is constructed with at least some magnetically attractive metal such that the magnet in lower assembly 14 attracts and holds the magnetically attractive metal of upper assembly 14.

In an alternative embodiment magnets (not shown) are provided at wall 72 and at wall 70 and are aligned along common axis 24. The magnets are correspondingly placed such that when lower assembly 14 is attached to the upper assembly 12 the magnets are adjacent each other and magnetically attracted to each other.

In an alternative embodiment, the magnetic coupler and rotation connection structure of upper assembly 12 described herein may be installed on the lower assembly 14 and the magnetic coupler and rotation connection structure of lower assembly 14 described herein correspondingly installed on upper assembly 12.

Retrofit Embodiment and Method

An alternate embodiment of the present invention consists of a method to retrofit an existing coaxial viscometer bob and bob shaft with a coupler 10.

Figure 9:
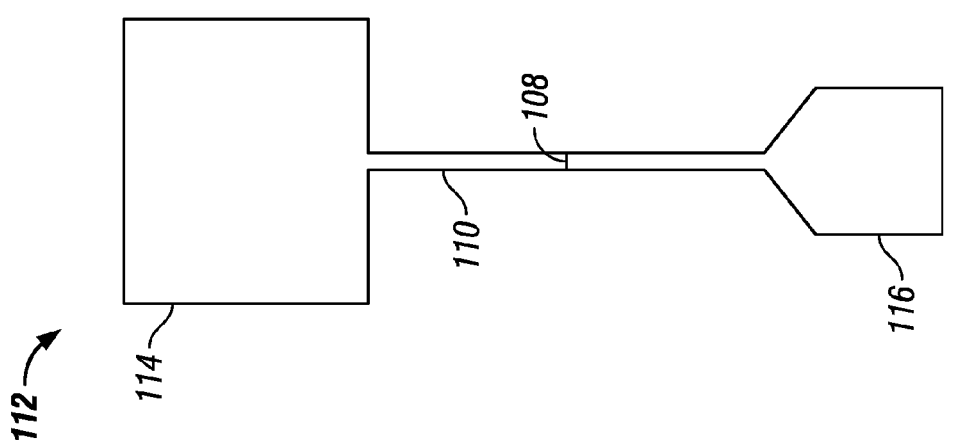
FIG. 9 is a diagram view of an example viscometer for retrofit application of a coupler.

Referring to FIG. 9, an upper bob shaft 110 is cut at a determined location below body 114 of existing viscometer 112 and above bob 116. Such cutting may be by saw, torch or other means. An example cutting point 108 is depicted.

Figure 10:
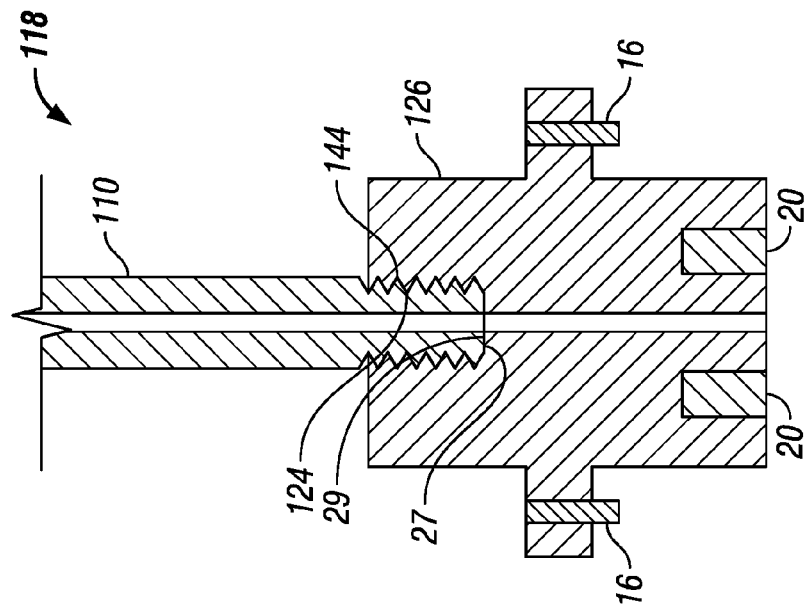
FIG. 10 is a cross-sectional view of a retrofit upper bob shaft and upper assembly of a retrofit coupler.

Referring now to FIG. 10, an exemplary upper assembly 118 is then attached to the upper bob shaft 110. In the exemplary embodiment of FIG. 10, external threading 144 is provided on the lower end of the upper bob shaft 110. As an example, on the existing viscometer 30 shown in FIG. 9 threading 144 would be provided just above the cutting point 108 after cutting is performed. Corresponding internal upper threading 124 is provided in upper body 126. Threading 144 and threading 124 are operable to fixedly attach upper body 126 to upper bob shaft 110. Other forms of attachment may be used provided a fixed connection is established with coaxial alignment of the upper bob shaft 110 and upper assembly 118.

As shown in the embodiment of FIG. 10, a hollow upper bob shaft 110 is provided. This embodiment, when used in conjunction with a hollow lower bob shaft 28 as depicted in FIG. 1, allows one or more wires or tubes to extend intermediate an upper end of bob shaft 110 and the bob 50. Accordingly, wiring may be connected to a thermocouple or other probe (not shown) provided in or proximate bob 116. Such wiring may be connected to an measurement device.

Upper assembly 118 of the embodiment shown in FIG. 7 corresponds with upper assembly 12 of the embodiment of FIGS. 1-5. Accordingly, lower assembly 14 of the embodiment of FIGS. 1-5 as previously described may be coupled with upper assembly 118 in the manner previously described.

A method of installing a coupler 10 on a pre-existing viscometer 112 includes: (1) a removal step, (2) an attachment preparation step, and (3) an attachment step. The removal step consists of removing the preexisting bob 50 from the preexisting bob shaft 110 of the preexisting viscometer 112. Appropriate removal methods including sawing the bob shaft 110 or heat detachment such as by cutting torch. The attachment preparation step consists of machining or otherwise preparing the preexisting bob shaft 50 so that it will couple with the upper assembly 118. An appropriate attachment preparation step comprises threading for threading attachment, machining for forced fit attachment, welding, or other appropriate method. The attachment step consists of attaching the coupler 10 to the preexisting bob shaft 110. Such attachment may be by threading, force fit, welding or other appropriate method.

Unless otherwise stated, each feature disclosed may be replaced by alternative features serving the same, equivalent, or similar purpose. Thus, unless expressly stated otherwise, each feature disclosed is one example only of a generic series of equivalent or similar features.

As used herein, "comprise" and "contain" and variations thereof mean including but not limited to.

Throughout the description and claims of this specification, the singular encompasses the plural unless the context otherwise requires. In particular, where the indefinite article is used, the specification is to be understood as contemplating plurality as well as singularity, unless the context requires otherwise.

All of the features disclosed in this specification (including any accompanying claims, abstract and drawings), and/or all of the steps of any method or process so disclosed, may be combined in any combination, except combinations where at least some of such features and/or steps are mutually exclusive.

Although various exemplary embodiments have been shown and described, the disclosure is not limited to the embodiments shown. Various changes or modifications may be made to the disclosed embodiments without departing from the true spirit and scope of the disclosure as contained within the scope of the appended claims. No single embodiment is representative of all aspects of the invention. It is understood that the invention is only limited by the claims and their equivalents.

We claim:

1. A coupler for a viscometer bob shaft comprising:
an upper assembly connected to an upper bob shaft;
a lower assembly attached to a lower bob shaft;
said lower assembly connectable to said upper assembly by at least one magnet provided in at least one of said upper assembly and said lower assembly and at least one magnet attracted material in said other of said upper assembly and said lower assembly;
a rotation connection between said upper assembly and said lower assembly comprising at least one first face on said upper assembly and at least one second face on said lower assembly;
said at least one first face proximate said at least one second face in a coupled orientation;
said first face and said second face configured to cooperatively induce rotation of said upper assembly when said lower assembly is rotated;
said coupler having a central rotation axis;
said at least one first face comprising other than a cylindrical wall face coaxially aligned with said central rotation axis; and
said at least one second face comprising other than a cylindrical wall face coaxially aligned with said central rotation axis.

2. A coupler of claim 1, further comprising
said at least one magnet comprising a first magnet; and
said at least one magnet attracted material comprising a second magnet.

3. A coupler of claim 1, further comprising:
said at least one magnet proximate said at least one magnet attracted material in a coupled orientation.

4. A coupler of claim 1, further comprising:
said at least one first face comprising at least one flat side face; and
said at least one second face comprising at least one flat side face.

5. A coupler of claim 1, further comprising:
said rotation connection between said upper assembly and said lower assembly comprising at least one insert pin extending from one of said upper assembly and said lower assembly, and at least one pin receiver in the other of said upper assembly and said lower assembly; and
said at least one insert pin received in said at least one pin receiver in a coupled orientation.

6. A coupler of claim 1, further comprising:
at least one of said upper assembly and said lower assembly having an external wall;
the other of said upper assembly and said lower assembly having a recess;
said recess defining a recess wall;
at least a segment of said external wall slideably insertable in said recess; and
said external wall abutting said recess wall in a coupled orientation.

7. A coupler of claim 6, further comprising:
at least a portion of said external wall defining said first face;
at least a portion of said recess wall defining said second face; and
said first face abutting said second face in a coupled orientation.

8. A coupler of claim 7, further comprising:
at least a portion of said external wall defining two parallel flat wall faces;
at least a portion of said recess wall defining a channel having two parallel flat recess wall faces; and
each said flat wall faces abutting a corresponding recess wall face in a coupled orientation.

9. A coupler of claim 6, further comprising:
a flange extending from one of said upper assembly and said lower assembly;
said flange having a flange surface;
at least one insert pin extending from said flange surface;
a contact surface provided on the other of said upper assembly and said lower assembly;
at least one pin receiver provided in said contact surface; and
said at least one insert pin received in said pin receiver and said contact surface abutting said flange surface in a coupled orientation.

10. A coupler of claim 1, further comprising:
said upper bob shaft extending through said upper assembly.

11. A coupler of claim 10, further comprising:
an upper bob shaft extension extending below said upper assembly;
an opening is provided in said lower assembly; and
said upper bob shaft extension received in said opening in a coupled orientation.

12. A coupler of claim 1, further comprising:
a flange extending from one of said upper assembly and said lower assembly;
said flange having a flange surface;
at least one insert pin extending from said flange surface;
a contact surface provided on the other of said upper assembly and said lower assembly;
at least one pin receiver provided in said contact surface; and
said at least one insert pin received in said pin receiver and said contact surface abutting said flange surface in a coupled orientation.

13. A coupler for a viscometer bob shaft comprising:
an upper assembly connected to an upper bob shaft;
a lower assembly attached to a lower bob shaft;
said lower assembly connectable to said upper assembly by at least one magnet provided in at least one of said upper assembly and said lower assembly and at least one magnet attracted material in said other of said upper assembly and said lower assembly;
a rotation connection between said upper assembly and said lower assembly comprising at least one insert pin extending from one of said upper assembly and said lower assembly, and at least one pin receiver in the other of said upper assembly and said lower assembly; and
said at least one insert pin received in said at least one pin receiver in a coupled orientation;
said upper assembly including an upper body;
said lower assembly including a lower body;
at least one of said upper body and said lower body comprising an insert body;
the other of said upper body and said lower body having a socket for slideably receiving said insert body;
said insert body having an external wall;
said socket having a socket recess wall;
said external wall abutting said socket recess wall in a coupled orientation.

14. A coupler of claim 13, further comprising
said at least one magnet comprising a first magnet; and
said at least one magnet attracted material comprising a second magnet.

15. A coupler of claim 14, further comprising:
a flange extending from one of said upper assembly and said lower assembly;
said flange having a flange surface;
said at least one insert pin extending from said flange surface;
a contact surface provided on the other of said upper assembly and said lower assembly;
said at least one pin receiver provided in said contact surface; and
said at least one insert pin received in said pin receiver and said contact surface abutting said flange surface in a coupled orientation.

16. A coupler of claim 13, further comprising:
said rotation connection between said upper assembly and said lower assembly comprising at least one first face on said insert body and at least one second face on said socket recess wall;
said at least one first face proximate said at least one second face in a coupled orientation: and
said first face and said second face configured to cooperatively induce rotation of said upper assembly when said lower assembly is rotated.

17. A coupler of claim 13, further comprising:
at least a portion of said external wall defining two parallel flat wall faces;
at least a portion of said socket recess wall defining two parallel flat recess wall faces; and
each said flat wall faces abutting a corresponding socket recess wall face in a coupled orientation.

18. A coupler of claim 13, further comprising:
a flange extending from one of said upper assembly and said lower assembly;
said flange having a flange surface;
said at least one insert pin extending from said flange surface;
a contact surface provided on the other of said upper assembly and said lower assembly;
said at least one pin receiver provided in said contact surface; and
said at least one insert pin received in said pin receiver and said contact surface abutting said flange surface in a coupled orientation.

* * * * *